US007918225B2

(12) United States Patent
Dolezal et al.

(10) Patent No.: US 7,918,225 B2
(45) Date of Patent: Apr. 5, 2011

(54) BREATHING AIR FILTRATION DEVICES

(75) Inventors: David M. Dolezal, Edina, MN (US); John D. Wilder, Brooklyn Park, MN (US); Daniel M. Gelfman, Minnetonka, MN (US)

(73) Assignee: AirWave, Inc., Scottsdale, AZ (US)

( * ) Notice: Subject to any disclaimer, the term of this patent is extended or adjusted under 35 U.S.C. 154(b) by 404 days.

(21) Appl. No.: 11/238,672

(22) Filed: Sep. 29, 2005

(65) Prior Publication Data

US 2008/0023007 A1 Jan. 31, 2008

Related U.S. Application Data

(63) Continuation-in-part of application No. 11/077,784, filed on Mar. 11, 2005, which is a continuation-in-part of application No. 10/804,995, filed on Mar. 19, 2004, now Pat. No. 7,156,098.

(51) Int. Cl.
*A61M 16/00* (2006.01)

(52) U.S. Cl. ......... 128/206.11; 128/205.27; 128/205.29; 128/207.18

(58) Field of Classification Search ............. 128/206.11, 128/205.27, 205.29, 207.13, 207.18, 201.18
See application file for complete search history.

(56) References Cited

U.S. PATENT DOCUMENTS

| | | | |
|---|---|---|---|
| 480,505 A * | 8/1892 | Midgley et al. | 128/204.13 |
| 533,880 A | 2/1895 | Forne | |
| 701,538 A | 6/1902 | Carence | |
| 813,425 A | 2/1906 | Hill | |
| 1,071,015 A | 8/1913 | Adler | |
| 1,175,799 A | 3/1916 | Niessner | |
| 1,322,375 A | 11/1919 | Un | |
| 1,508,890 A | 9/1924 | Lasseaux | |
| 1,520,930 A | 12/1924 | Calhoun | |
| 1,823,094 A | 9/1931 | Dylong | |
| 2,046,664 A | 7/1936 | Weaver | |
| 2,057,397 A | 10/1936 | Clauss | |

(Continued)

FOREIGN PATENT DOCUMENTS

AU 2006100453 7/2006

(Continued)

OTHER PUBLICATIONS

Derwent Pat-No. JP401160572A; Document-Identifier: JP 01160572 A; Jun. 23, 1989, Tate, Pollen Protection tool for nose, abstract.*

(Continued)

*Primary Examiner* — Steven O Douglas
*Assistant Examiner* — Clinton Ostrup
(74) *Attorney, Agent, or Firm* — Dorsey & Whitney LLP; Nathan J. Witzany

(57) ABSTRACT

A nasal air filtration device includes a pair of either planar or concave-convex filters, a support structure incorporating a pair of generally annular bases or sleeves for supporting the filters, and a bridge that couples the bases or sleeves to maintain them in a desired spaced-apart relation and to determine a desired angular relationship. The support structure is insertable into the nasal cavities to position the filters within corresponding nasal cavities. Flexible rims maintain the support structure and the filters in spaced-apart relation to the surrounding nasal wall. The rims conform to surrounding nasal tissue to form seals. The rims can be selectively inclined to facilitate insertion and resist accidental removal. In certain embodiments the device is combined with a filter that covers the mouth to provide an air filtration system.

14 Claims, 7 Drawing Sheets

Fig. 21

U.S. PATENT DOCUMENTS

| | | | |
|---|---|---|---|
| 2,097,846 | A | 11/1937 | Clauss |
| 2,151,227 | A | 3/1939 | Pawelek |
| 2,162,583 | A | 6/1939 | Kjellsson |
| 2,277,390 | A | 3/1942 | Crespo |
| 2,433,565 | A | 12/1947 | Korman |
| 2,535,155 | A | 12/1950 | Pandorf |
| 2,672,138 | A | 3/1954 | Pomeroy |
| 2,751,906 | A | 6/1956 | Irvine |
| 2,777,442 | A | 1/1957 | Zelano |
| 2,890,695 | A | 6/1959 | Safstrom |
| 3,451,392 | A | 6/1969 | Cook et al. |
| 3,457,917 | A | 7/1969 | Mercurio |
| 3,463,149 | A | 8/1969 | Albu |
| 3,722,509 | A | 3/1973 | Nebel |
| 3,747,597 | A | 7/1973 | Olivera |
| 3,884,223 | A | 5/1975 | Keindl |
| 3,905,335 | A | 9/1975 | Kapp |
| 4,030,491 | A | 6/1977 | Mattila |
| 4,052,983 | A | 10/1977 | Bovender |
| D251,017 | S | 2/1979 | Amezcua |
| 4,220,150 | A | 9/1980 | King |
| 4,221,217 | A | 9/1980 | Amezcua |
| 4,267,831 | A | 5/1981 | Aquilar |
| 4,327,719 | A | 5/1982 | Childers |
| 4,401,117 | A | 8/1983 | Gershuny |
| 4,573,461 | A | 3/1986 | Lake |
| 4,984,302 | A | 1/1991 | Lincoln |
| 5,117,820 | A | 6/1992 | Robitaille |
| 5,392,773 | A | 2/1995 | Bertrand |
| 5,417,205 | A | 5/1995 | Wang |
| 5,568,808 | A | 10/1996 | Rimkus |
| 5,746,200 | A | 5/1998 | Draenert |
| 5,775,335 | A | 7/1998 | Seal |
| 5,787,884 | A | 8/1998 | Tovey |
| 5,890,491 | A | 4/1999 | Rimkus |
| 6,015,425 | A | 1/2000 | Altadonna, Jr. |
| 6,109,262 | A | 8/2000 | Tovey |
| D430,667 | S | 9/2000 | Rome |
| 6,119,690 | A | 9/2000 | Pantaleo |
| 6,183,493 | B1 | 2/2001 | Zammit |
| 6,213,121 | B1 | 4/2001 | Cardarelli |
| 6,216,694 | B1 | 4/2001 | Chen |
| D451,193 | S | 11/2001 | McCormick |
| 6,386,197 | B1 | 5/2002 | Miller |
| 6,484,725 | B1 | 11/2002 | Chi |
| 6,494,205 | B1 | 12/2002 | Brown |
| 6,561,188 | B1 | 5/2003 | Ellis |
| 6,584,975 | B1 | 7/2003 | Taylor |
| 6,701,924 | B1 | 3/2004 | Land, Jr. et al. |
| 6,962,156 | B2 | 11/2005 | Michaels |
| 6,971,387 | B2 | 12/2005 | Michaels |
| 6,971,388 | B1 | 12/2005 | Michaels |
| 6,978,781 | B1 | 12/2005 | Jordan |
| 7,156,098 | B2 | 1/2007 | Dolezal et al. |
| D571,457 | S | 6/2008 | Dolezal |
| D572,360 | S | 7/2008 | Dolezal |
| D572,361 | S | 7/2008 | Noce |
| D575,397 | S | 8/2008 | Noce |
| D595,848 | S | 7/2009 | Dolezal et al. |
| 2003/0106555 | A1 | 6/2003 | Tovey |
| 2003/0106556 | A1 | 6/2003 | Alperovich et al. |
| 2003/0136409 | A1 | 7/2003 | Seo |
| 2003/0209145 | A1 | 11/2003 | Soper |
| 2004/0055603 | A1 | 3/2004 | Bruce |
| 2004/0079814 | A1 | 4/2004 | Altadonna, Jr. |
| 2004/0194784 | A1 | 10/2004 | Bertrand |
| 2004/0211425 | A1 | 10/2004 | Wang |
| 2004/0261798 | A1 | 12/2004 | Rimkus |
| 2005/0061325 | A1 | 3/2005 | Michaels |
| 2005/0066972 | A1 | 3/2005 | Michaels |
| 2005/0066973 | A1 | 3/2005 | Michaels |
| 2005/0205095 | A1 | 9/2005 | Dolezal |
| 2005/0211250 | A1 | 9/2005 | Dolezal et al. |

FOREIGN PATENT DOCUMENTS

| | | | | |
|---|---|---|---|---|
| CN | 2236341 | Y | | 10/1996 |
| CN | 2250782 | Y | | 4/1997 |
| DE | 201 01 539 | U1 | | 7/2001 |
| EP | 1 340 522 | A2 | | 9/2003 |
| JP | S49-94491 | | | 8/1974 |
| JP | S52-164394 | | | 12/1977 |
| JP | S55-148761 | | | 10/1980 |
| JP | S60-171450 | | | 11/1985 |
| JP | S61-228883 | | | 10/1986 |
| JP | 1-160572 | A | * | 6/1989 |
| JP | H2-126668 | | | 10/1990 |
| WO | WO 99/11326 | | | 3/1999 |
| WO | WO 0141629 | A2 | * | 6/2001 |
| WO | WO 2005/092004 | | | 10/2005 |
| WO | WO 2007/139890 | | | 12/2007 |

OTHER PUBLICATIONS

Merriam-Webster Online Dictionary definition of "machine" (http://www.merriam-webster.com/dictionary/machine), Apr. 8, 2010.*

T. J. O'Meara, et al., "The reduction of rhinitis symptoms by nasal filters during natural exposure to ragweed and grass pollen", Allergy 2005: 60: 529-532.

Medical Device Company Focused Initially on Preventing Hay Fever, The University of Sydney Business Liaison Office, Commercialisation; *Forum & Fair of Ideas*; Sydney Mar. 26-28, 2003.

Webster's New World Dictionary, Third College Edition, 1988, p. 155 & 1438 definitions for body and tubular.

"Nose Filters, Better Breathers", Better Breathers™ [retrieved on Sep. 14, 2010] Retrieved from http://www.betterbreathers.com/index.html.

"Breathing Allergy Relief / Allergy Relief Pregnancy", Breathe-Ezy Nasal Filters®, [retrieved on Sep. 14, 2010], Retrieved from http://breathe-ezy.com.au/.

"SHS Nose Filters Ring", Diamond Life Group, [retrieved on Sep. 14, 2010], Retrieved from http://www.diamondlife.net.au/product.

* cited by examiner

BREATHING AIR FILTRATION DEVICES

CROSS REFERENCE TO RELATED APPLICATIONS

This is a continuation-in-part of application Ser. No. 11/077,784, filed Mar. 11, 2005, which is a continuation-in-part of application Ser. No. 10/804,995, filed Mar. 19, 2004, now U.S. Pat. No. 7,156,098.

BACKGROUND OF THE INVENTION

The present invention relates to devices and systems for filtering ambient air as it is inhaled, and more particularly to filtration devices and systems that employ filtering media and filtering components insertable into the nasal cavities.

There is an increasing need for effective filtration of breathing air, to reduce inhaled quantities of particulates and contaminants such as dust and pollen. In cities and other densely populated regions, there is a greater need for filtering pollutants generated by industrial and vehicle emissions. Certain specialized environments entail a greater risk of contamination in ambient air, e.g. construction sites and mines with respect to particulate matter, and hospitals with respect to viral and bacterial agents.

These concerns have led to development of a wide variety of masks, typically designed to cover the nose and mouth of the user. These masks frequently are ineffective due to perimeter leakage between the mask and face. Individuals who might benefit from the masks frequently refuse to wear them, due to discomfort or dissatisfaction with the appearance of the mask. Moreover, the masks tend to trap exhaled carbon dioxide, especially when the mask includes a fine (microporous) filter and forms a-tight seal against the face. The longer the mask is worn, the greater is the tendency for buildup of carbon dioxide. The user, inhaling increasing amounts of carbon dioxide, is subject to headaches, drowsiness, and nausea, with prolonged exposure causing more severe effects.

To address these concerns, a variety of filtering devices have been proposed for insertion into nasal cavities. For example, U.S. Pat. No. 216,694 (Chen) shows a filter with a pair of plug units joined by a belt section, each plug unit receiving a filter. Similarly, U.S. Pat. No. 2,433,565 (Korman) describes a filter in which nostril inserts are joined by a bridge piece. Each insert contains a filter and a porous cone that can be used to deliver medication. In these devices, cylindrical or conical support structures surround the filtering media and press against the inside surface of the nasal wall and septum, frictionally retaining the filter. This support may be supplemented by an adhesive. In either event the supporting structure, which is impermeable to air flow, presses against the nasal wall and tends to mat the turbinates and nose hairs, thus diminishing the capacity of the nostril to trap particles, and warm and moisten incoming air. The filtering devices may satisfactorily perform the particle trapping function, but are not well adapted to warm and moisten the incoming air.

In an alternative approach, U.S. Pat. No. 5,392,773 (Bertrand) discloses a filter mounted outside the nasal cavities, secured to the nasal wall with an adhesive. The appearance of the filter, and the need for an adhesive, are disadvantages to this approach.

Further, regardless of whether the foregoing nasal filters are mounted outside the nose or inserted into the nasal cavities, they frequently are inconvenient to use and uncomfortable to wear, and fail to provide a reliable sealing engagement with nasal or facial tissue to ensure that incoming air passes through the filtering media. Finally, the nasal filters afford no protection against intentional or inadvertent inhaling through the mouth.

Therefore, it is an object of the present invention to provide a breathing air filtration device with filtering media and their supporting structure insertable into the nasal cavities, adapted to form an effective seal against surrounding nasal tissue and maintain the filtering media securely against inadvertent removal, without unduly diminishing the user's comfort.

Another object is to provide a filtration device adapted to maintain filtration media and their support structure inside a nasal cavity in spaced-apart relation to the nasal wall, to provide effective filtration while reducing interference with the particle trapping, air warming and air moistening functions of the nasal interior wall.

A further object is to provide a filtration system that effectively filters air entering the nose and mouth, and at the same time considerably reduces the volume available for trapping exhaled carbon dioxide as compared to masks that cover the nose and mouth.

Yet another object is to provide nasal filters and breathing air filtration systems that are convenient to use, yet afford better sealing against nasal and facial tissue for more effective filtration.

BRIEF SUMMARY OF THE INVENTION

To achieve these and other objects, there is provided a breathing air filtration device. The device includes a concave-convex first filtering medium having a first rim at an open proximal end thereof defining a first opening surrounded by the first rim. A concave-convex second filtering medium has a second rim at an open proximal end thereof defining a second opening surrounded by the second rim. The filtration device has a support structure including a first base member coupled integrally with respect to the first rim to support the first filtering medium, and a second base member coupled integrally to the second rim to support the second filtering medium. A connecting member is coupled integrally to the first base member and the second base member and extends between the base members. The support structure base members are positionable at the nasal cavity entrance, with the connecting member spanning the septum. This places each of the first and second filtering media in a working position in which the filtering medium projects distally into an associated one of the nasal cavities. Thus, air entering each nasal cavity passes through the associated one of the first and second openings, and further passes through the associated one of the first and second filtering media.

Preferably, each filtering medium in its working position is spaced apart from the septum and from the nasal wall defining the associated nasal cavity. This result may be achieved by using a filtering medium that is substantially self-supporting, or by disposing an open frame between a more pliable filtering medium and the nasal wall. In either event, this arrangement provides increased comfort, and facilitates the flow of incoming air along the inside surface of the nasal wall, to effectively warm and moisturize the air when the filtering device is in place.

The filtering media can have elliptical and ellipsoidal shapes, to more readily conform to the nostrils and nasal cavities. Alternatively, each filtering medium can have a truncated-conical shape, preferably modified to exhibit elliptical profiles in transverse planes.

Conical or ellipsoidal filtering media afford increased area available for filtration as compared to filtering media with planar surfaces at the nasal cavity entrance. This advantage can be appreciated when considering the surface area of a hemisphere, as compared to a disk of the same radius. The hemisphere surface area is twice as large. The ellipsoidal and elliptical/conical filtering media can be configured to enhance the advantage, providing effective surface areas more than twice the area of the entrance to the nasal cavity.

The present invention may be embodied in a two-stage device, in which a first screening component is mounted with respect to the first base member and disposed proximally of the first filtering medium, and a second screening component is similarly mounted with respect to the second base member. The screening component can comprise a relatively coarse (larger porosity) activated charcoal filter intended to remove odors and larger particles. This prevents the larger particles from reaching the downstream filtering media, extending their useful life.

In certain environments, it is vital to insure against inhaling contaminants through the mouth as well as the nose. To this end, the device is augmented with a third base member positionable against the face in surrounding relation to the mouth to form an opening through which air can enter the mouth, and a third filtering medium mounted with respect to the third base member and dispose over the opening. If desired, the third filtering medium can be concaved-convex and project away from the mouth in the proximal direction. A flexible band or other retainer is used to releasably maintain the third base member against the user's face.

As compared to a mask filter covering the nose and mouth, the combination of separate nose and mouth filters is less cumbersome, less prone to leakage at the filtering device perimeter, and has a smaller enclosed volume near the face, and therefore is less prone to accumulation of exhaled carbon dioxide. If the user inhales substantially exclusively through the nose, problems due to carbon dioxide accumulation are avoided altogether.

In accordance with another aspect of the invention, there is provided a nasal air filtering device. The device includes a first filter and a second filter, both having respective first and second proximal ends and adapted for insertion into a nasal cavity. The device also includes a filter support structure including a first base member coupled with respect to the first proximal end and supporting the first filter, a second base member coupled with respect to the second proximal end and supporting the second filter, and a connecting member integrally coupled to the base members and extended between the base members. The base members of the filter support structure are positionable at the entrances to the nasal cavities, with the connecting member spanning the septum, thus to place each filter in a working position in which the filter projects distally into an associated one of the nasal cavities, and is spaced apart from the nasal wall that defines the associated cavity, thus to define a passage for accommodating air flow between the filter and the nasal wall.

If desired, each filter can be concave in the proximal direction and convex in the distal direction. The filter may be self-supporting and thus stand spaced apart from the nasal wall by virtue of its coupling to the associated base member. Alternatively, an open frame can be coupled to the base member and disposed between the filter and the nasal wall, to maintain the desired spacing.

Another aspect of the present invention is a nasal air filter support device. The device includes a first support member comprising a first tubular body having an anterior end and a posterior end, and defining a first longitudinal passageway therethrough, and further comprising a first rim disposed circumferentially about the first tubular body and extending radially outwardly from the first tubular body. The device includes a second support member comprising a second tubular body having an anterior end and a posterior end, and defining a second longitudinal passageway therethrough. The second support member further comprises a second rim disposed circumferentially about the second tubular body and extending radially outwardly from the second tubular body. A connecting member is integrally coupled to the first tubular body and second tubular body. Each of the tubular bodies is insertable by the anterior end thereof into an associated one of the nasal cavities with the associated rim being adapted to form a surface engagement with the nasal wall and septum defining the associated nasal cavity. The associated rim further is elastically deformable and tends to conform to the surrounding nasal wall and septum over an area of the surface engagement, to substantially form a seal along the area and to support the associated tubular body within the associated nasal cavity. Each of the first and second rims further is inclined in the radially outward direction toward the posterior end of its associated tubular body.

A further aspect of the present invention is a nasal air treatment appliance. The appliance includes a first support member comprising a first tubular body having an anterior end and a posterior end, and defining a first passageway to accommodate a longitudinal flow of air therethrough. The first support member further has a pair of rims comprising a first rim surrounding the first tubular body and extending radially outwardly from the first tubular body, and a second rim surrounding the first tubular body in longitudinally spaced apart relation to the first rim and extending radially away from the first tubular body. The appliance includes a second support member comprising a second tubular body having an anterior end and a posterior end and defining a second passageway to accommodate a longitudinal flow of air therethrough. The second support member further has a pair of rims comprising a third rim surrounding the second tubular body and extending radially away from the second tubular body, and a fourth rim surrounding the second tubular body in longitudinally spaced apart relation to the third rim and extending radially away from the second tubular body. A connecting member is integrally coupled to the first and second tubular bodies. Each pair of the rims is adapted to form a surface engagement with the nasal wall and septum defining an associated one of the nasal cavities, responsive to an insertion of their associated tubular body longitudinally into the associated nasal cavity by the anterior end thereof. The rims thereby support and maintain the associated tubular body within the associated nasal cavity in spaced apart relation to the nasal wall and septum.

Another aspect of the present invention is a breathing air filtration system. The system includes a first tubular body having an anterior end and a posterior end, and defining a first passageway to accommodate a longitudinal flow of air therethrough. The system includes a second tubular body having an anterior end and a posterior end, and defining a second passageway to accommodate a longitudinal flow of air therethrough. The system further includes a frame member positionable against the face in surrounding relation to the mouth and defining an air flow opening coincident with the mouth when the frame is so positioned. A connecting member is integrally coupled to the first tubular body, the second tubular body and the frame member, and is adapted to locate the first and second tubular bodies within the nasal cavities when the frame member is so positioned.

Thus in accordance with the present invention, a filtration device insertable into the nasal cavities is easy to use, has a minimal impact on the appearance of the user, and provides more effective and longer-lasting filtration. Improved performance arises in part from the retention of air warming and moisturizing capability when the filtering media are maintained in the spaced-apart relation to the nasal walls. Improved performance also can arise from an enlarged surface area available for filtration, due to a concave-convex shape or truncated conical of the filtering media, and further if desired by forming the media with pleats or corrugations. Finally, the nasal filter can be combined with a filter covering the mouth to provide a filtration system which, compared to a conventional mask, is less prone to perimeter leakage and accumulation of exhaled carbon dioxide.

BRIEF DESCRIPTION OF THE DRAWINGS

For a further appreciation of the above and other features and advantages, reference is made to the following detailed description and to the drawings, in which.

DETAILED DESCRIPTION OF THE INVENTION

Figure 1:
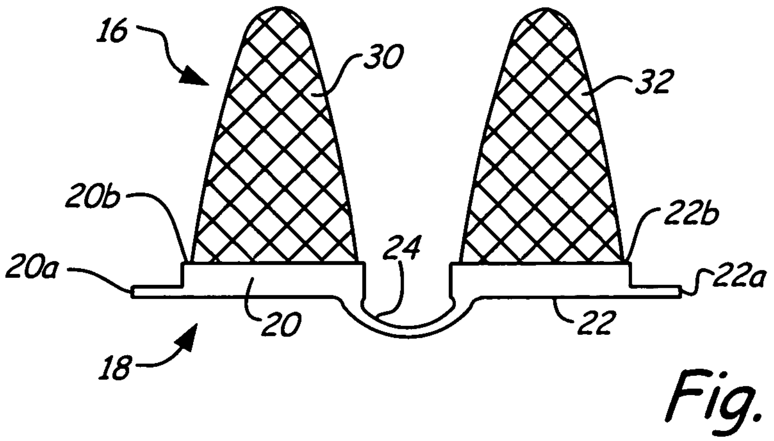
FIG. 1 is a forward elevational view showing a nasal air filtration device constructed in accordance with the present invention.

Turning now to the drawings, there is shown in FIG. 1 a nasal air filtering device 16 insertable into the nasal cavities to filter ambient air as it is inhaled by the user. Device 16 includes a unitary support structure or panel 18, preferably formed of a hypo-allergenic material such as polyvinyl chloride (PVC) or polyurethane. The panel is structurally self-supporting and further is flexible and compliant so that it readily conforms to the anterior surface of the nose, in particular the anterior nares and septum, when device 16 is in use.

Figure 2:
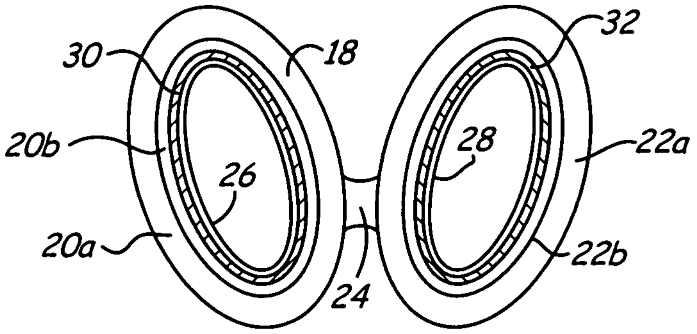
FIG. 2 is a sectional view taken along the line 2-2 in FIG. 1.
Figure 3:
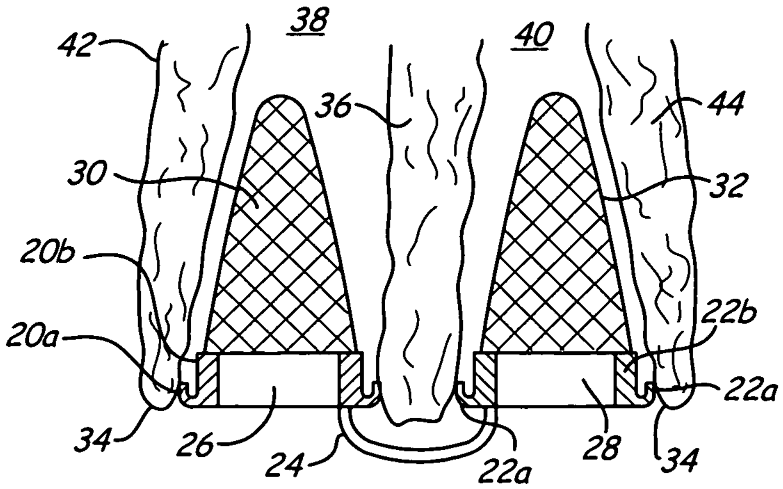
FIG. 3 is a schematic view of the device in use.

Panel 18 includes a base 20, an opposite base 22, and a connecting member or bridge 24 coupled to the bases to maintain the bases spaced apart from one another a desired distance. Each of the bases is annular—more precisely, generally annular in sense that its profile is somewhat elliptical rather than circular. Bases 20 and 22 have respective closed or endless perimeter regions **20*a* and 22*a*, and shoulders 20*b* and 22*b* that surround openings through the base, to admit air when the device is in use. As seen in FIGS. 2 and 3, openings 26 and 28 are formed through bases 20 and 22, respectively. Bridge 24 is relatively narrow to provide bending flexibility along the bridge. Base perimeter regions 20*a*/22*b* are thin and flexible, while shoulders 20*b*/22*b*** are more rigid.

A generally conical filtering medium or filter 30 is mounted on base 20, and a similar filter 32 is mounted on base 22. Each filter is mounted to its associated base along a generally annular proximal edge or rim and extends away from the base to a distal apex. In use, filters 30 and 32 extend distally into the nasal cavities. Each of the filters can be attached to its associated one of shoulders **20*b* and 22*b*** with a suitable adhesive.

Filters 30 and 32 can be formed from a wide variety of materials, and further can be formed with a wide (several orders of magnitude) range of porosities, depending on the nature of the contaminants to be filtered. Materials and porosities can be selected in accordance with National Institute for Occupational Safety and Health (NIOSH) classifications, e.g. dusts, mists and fumes (DMF), or high-efficiency particulate air (HEPA) filters. Preferred materials include the electrostatic filtration media available under the name "Technostat" from Hollingsworth & Vose Air Filtration, Ltd. of Kentmere, Cumbria, United Kingdom. Suitable materials include natural fabrics such as cotton, and polymeric materials such as nylon, polyethylene and polypropylene. Hypo-allergenic materials such as PVC and polyurethane also may be employed. Each of the filters has a substantially uniform thickness, and in general has a truncated conical shape, although differing from a precise truncated cone in two respects. With reference to filter 30, the distal end near the apex forms a rounded dome, rather than a transverse plane. Second, profiles of filter 30 taken in transverse planes are elliptical rather than circular, to provide a filter shape that better conforms to the nasal cavity. Filter 32 is similarly shaped.

FIG. 2 shows the elliptical profiles of filters 30 and 32, and further illustrates a preferred angular orientation of the filters and bases relative to each other. Bridge 24 maintains the preferred orientation as well as maintaining the bases and filters in a desired spaced-apart relation to each other. In this orientation, the long or lengthwise axes of the respective ellipses are not parallel, but maintained at an angle, e.g., about 30 degrees. As a result, filters 30 and 32 are angularly oriented in a manner that better conforms to the relative angular orientation of the nostrils and nasal cavities, thus to provide a closer, more comfortable fit of the filters within the nasal cavities. The bridge is sufficiently flexible to allow limited adjustment of the angle to suit the person wearing the device.

As seen in FIG. 3, perimeter regions **20*a* and 22*a* are positionable inside of the entrances 34 to nasal cavities 38 and 40, with bridge 24 spanning the septum 36. This forms a close fit in which the perimeter regions tend to conform to the nasal cavity entrances, forming a contiguous surface engagement that frictionally maintains each filter within its associated nasal cavity, and preferably provides a seal. Shoulders 20***b* and 22*b* extend into the nasal cavities 38 and 40, spaced apart from the nasal wall interior. This places each of filters 30 and 32 in a working position in which the filter extends distally into its associated nasal cavity: filter 30 into nasal cavity 38, and filter 32 into nasal cavity 40. The width (radial dimension) and thickness (axial dimension) of perimeter regions 20*a* and 22*a* can vary with the material forming panel 18. In general, these dimensions are selected to provide each perimeter region with sufficient bending flexibility to conform to the nasal wall near the entrance to the nasal cavity and form the desired seal, and also with sufficient structural rigidity and strength to frictionally support the associated base and filter in their associated nasal cavity. To facilitate this dual function, the perimeter regions can be tapered to provide a thickness that decreases in the radially outward direction.

As a result of this positioning, and the close fit between bases 20 and 22 and the nasal cavities, air entering nasal cavity 38 enters through opening 26 and passes through filter 30. Likewise, air enters nasal cavity 40 through opening 28, and proceeds through filter 32.

Bridge 24 sets the desired spacing between bases 20 and 22, and thus facilitates proper-positioning of filters 30 and 32 in their respective nasal cavities. The bridge also prevents over insertion of the filters by virtue of its contact with the septum, and remains easily accessible to the user desiring to remove filtering device 16 after use. Further, as best seen in FIG. 2, bridge 24 determines the desired relative angular orientation of bases 20 and 22, and thus of filters 30 and 32.

Filtering device 16 affords several advantages in comparison to the aforementioned conventional nasal filters. One of these arises from the concave-convex shape of filters 30 and 32. Each of the filters has a concave inside surface in the proximal (out of the nasal cavity) direction, and a convex exterior surface in the distal (into the nasal cavity) direction. As compared to a conventional arrangement including disk-shaped filters with surface areas comparable to openings 26 and 28, or higher volume filters that nonetheless are exposed only along openings such as 26 and 28, filters 30 and 32 have a much larger surface area available for filtration.

The magnitude of this difference can be understood when considering a filter shaped as a disk, compared to a filter having the same radius but shaped as a hemispherical shell. The surface area of the disk is 7Lr. The surface area of the hemispherical shell is 27Cr. The concavity in this instance doubles the surface area available for filtration. In the case of filters 30 and 32, this advantage is magnified, because the distance from the rim of each filter to its apex is considerably larger than the radius of the rim.

Another advantageous feature is the fact that filters 30 and 32 are structurally self-supporting and stand alone. They are not surrounded by an air-impermeable cylinder or barrel. Thus, inhaled air readily passes through the entire filter, not just at or near the apex.

In short, the concave-convex shape, in the absence of air-impermeable structure contacting and surrounding the filter, leads to a considerable increase in the surface area available for filtration. Even a slight degree of concavity can increase the available surface area by fifty percent. More preferably, the available surface area is at least doubled as compared to a planar filter at the nasal cavity entrance.

Another salient advantage resides in the spaced-apart relation of each filter to the nasal wall defining the nasal cavity. More particularly, filter 30, for example, is spaced apart from septum 36 and the nasal wall 42 that cooperates with the septum to surround the filter. Filter 32 likewise is spaced apart from septum 36 and a nasal wall 44. This spacing promotes the flow of inhaled air along the space between each filter and its surrounding nasal tissue. Perhaps more importantly, this spacing has a favorable impact on the capacity of the nasal wall to warm and moisten inhaled air. Nasal hairs and turbinates are exposed, rather than matted down by the filter, or by an air-impermeable cylinder surrounding a filter. Thus, filtering device 16, as compared to prior filters, more effectively preserves the air warming and air moisturizing capability of the nasal cavity.

Figure 4:
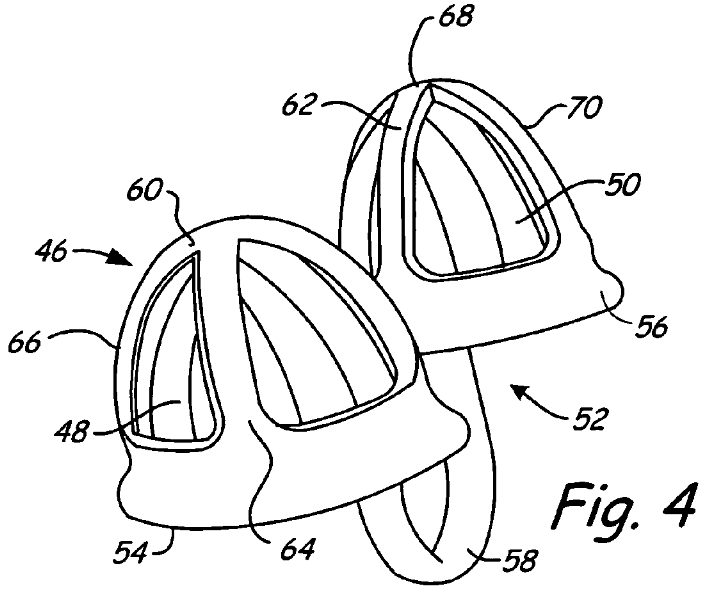
FIG. 4 is a perspective view of an alternative embodiment filtration device.
Figure 5:
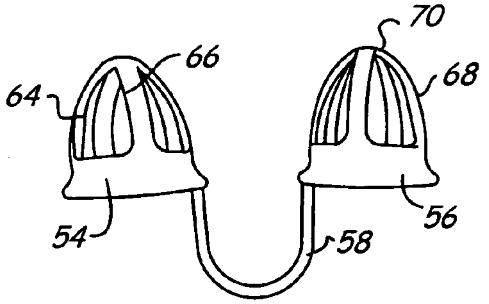
FIG. 5 is a forward elevation of the device shown in FIG. 4.

FIG. 4 illustrates an alternative filtering device 46 including a pair of ellipsoidal and corrugated filters 48 and 50 contained within a unitary support structure 52. The support structure is comparable to panel 18 in that it includes bases 54 and 56, and a bridge 58 coupled to the bases to maintain the desired spacing and angular relationship. Bridge 58 is u-shaped to allow a further distal insertion of the filters into their respective nasal cavity. Accordingly, filters 48 and 50 are shorter than filters 30 and 32, in terms of the axial distance between the rim and the apex. Further, however, an open frame 60 extends distally from base 54, and an open frame 62 extends distally from base 56. Frame 60 consists of arched, intersecting frame members 64 and 66, and frame 62 similarly consists of an intersecting pair of arched frame members 68 and 70. Each filter is contained within its associated base and frame. Frames 60 and 62 are relatively rigid, while the perimeter regions of bases 54 and 56 are more flexible to form a better seal against or near the anterior nares. Filters 48 and 50 need not be structurally self-supporting, due to the surrounding open frames.

Figure 6:
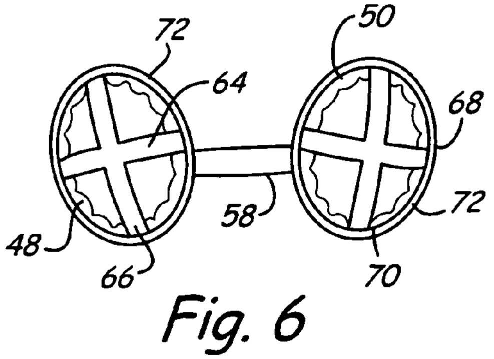
FIG. 6 is a top plan view showing the device of FIG. 4.

As perhaps best seen in FIG. 6, bridge 58 maintains bases 54 and 56, and thus filters 48 and 50 as well, in a preferred angular offset relative to each other. Multiple corrugations 72 are formed in each filter, beginning at the rim and extending upwardly toward the apex. The corrugations strengthen each filter in terms of increasing its rigidity. Further, the corrugated filter, as compared to a filter of the same size without the corrugations, has an increased surface area available for filtration.

Figure 7:
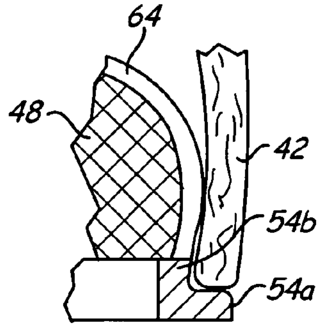
FIGS. 7 and 8 are schematic views illustrating operation of the device of FIG. 4.
Figure 8:
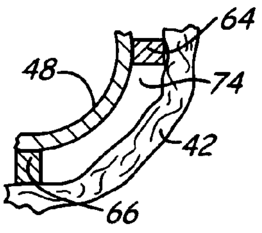

As seen from FIGS. 7 and 8, filter 48 is frictionally retained in its associated nasal cavity, by contact of frame members 64 and 66 and a shoulder 54*b* with the surrounding nasal wall. In this arrangement, which is different from that shown in FIG. 3, a perimeter region 54*a* is positioned against the anterior nares, and thus remains outside of the nasal cavity. The frame members cooperate to maintain their associated filter in spaced-apart relation to the surrounding nasal wall, forming a plurality of air flow passages between the filter and wall as indicated by a passage 74 formed by frame members 64 and 66. Filter 50 and base 56 are similarly supported. The passages facilitate a flow of inhaled air through each of filters 48 and 50 toward the nasal wall, then along the nasal wall and eventually past the filter. As before, this spacing facilitates the warming and moisturizing of inhaled air.

If desired, bases 54 and 56 can be formed with respective perimeter regions 54*a* and 54*b* sized for insertion into the nasal cavity entrances, to support their associated filters and bases in the manner illustrated in FIG. 3. In this approach, open frames 60 and 62 do not contribute to the frictional retention of the bases and filters, but instead tend to remain spaced apart from the interior nasal walls and septum. This arrangement requires a more precise sizing of the proximal regions of the bases. The primary advantage is that bases with bendable, compliant perimeter regions can form a satisfactory seal and frictional hold over a wider range of nasal cavity sizes and shapes.

Figure 9:
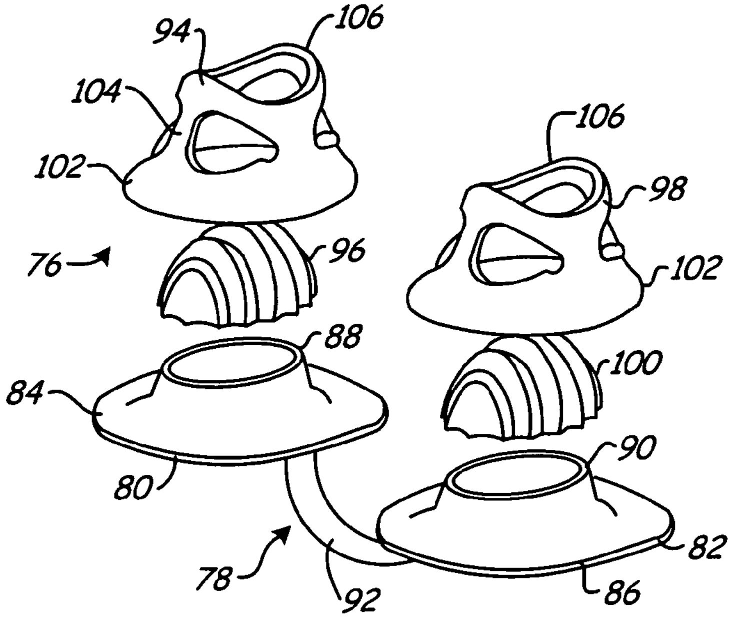
FIG. 9 is an exploded-parts view of another alternative embodiment filtration device.
Figure 10:
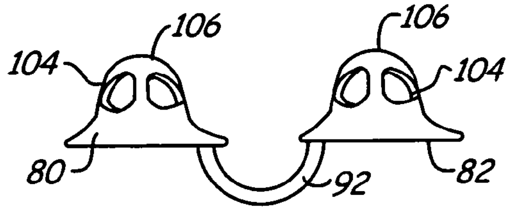
FIG. 10 is a forward elevational view showing the device of FIG. 9.
Figure 11:
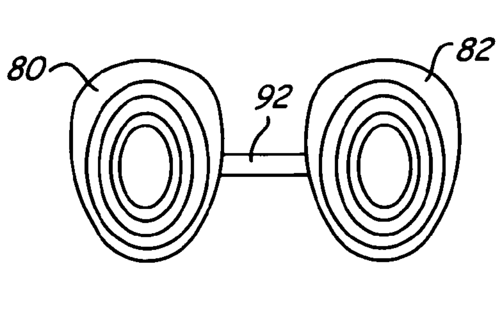
FIG. 11 is a top plan view of the device of FIG. 9.

FIG. 9 is an exploded-parts view of a further alternative embodiment nasal filtration device 76. Device 76 includes a filter support structure 78 having spaced apart bases 80 and 82 with relatively flat and generally annular perimeter portions 84 and 86 respectively, and respective raised and generally annular shoulders 88 and 90. The bases are coupled by an arcuate bridge 92.

An open-frame retainer 94, shown above base 80, can be removably press-fit onto the base to capture an ellipsoidal, corrugated filtering medium 96. An open-frame retainer 98 can be similarly coupled to base 82, to contain an ellipsoidal, corrugated filtering medium 100. Each of the retainers includes a generally annular bottom portion 102 sized and shaped for a press-fit coupling with the shoulder of its associated base. Each retainer further incorporates several frame members 104, shorter than frame members 64-70 and extending to an open top 106 of the retainer, rather than to an apex or junction of the frame members as with device 46. Frame members 104, like the frame members in device 46, contact the nasal wall to provide frictional mounting of the device, and maintain their associated filters in spaced-apart relation to the nasal wall to promote air flow between each retainer and the nasal wall that surrounds it.

Figure 12:
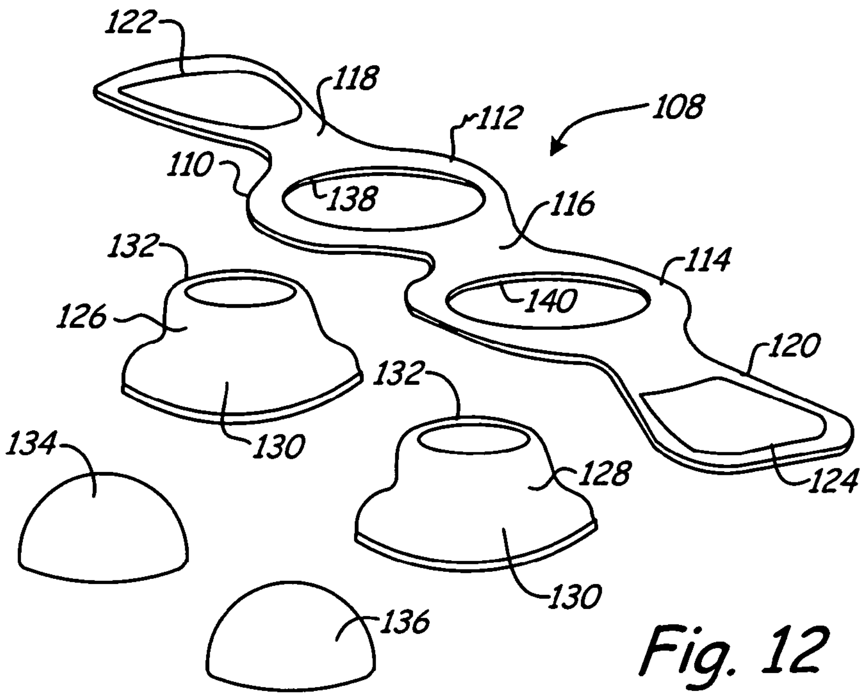
FIG. 12 is an exploded-parts view of another alternative embodiment filtration device.
Figure 13:
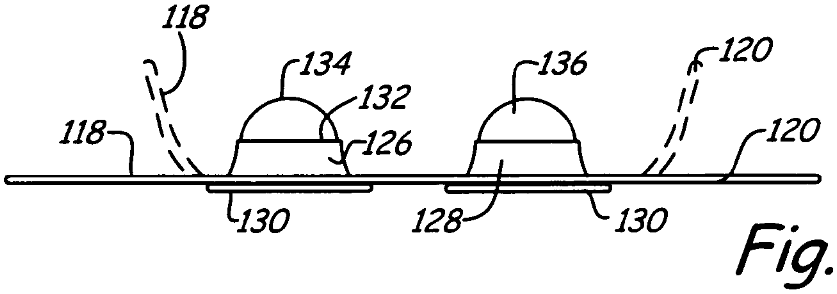
FIG. 13 is a forward elevational view of the device of FIG. 12.
Figure 14:
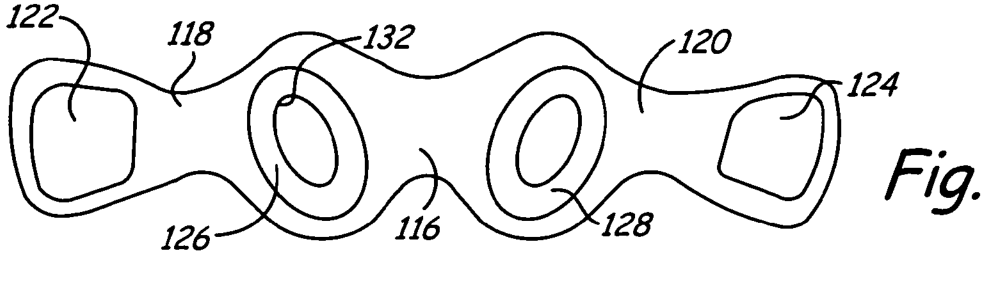
FIG. 14 is a top plan view of the device of FIG. 12.

FIGS. 12 through 14 show another alternative embodiment filtration device 108. The support structure is provided in the form of a flat, thin, flexible panel 110 that incorporates base portions 112 and 114 joined by a bridge portion 116. The panel further incorporates a tab 118 extending away from base portion 112, and a tab 120 extending in the opposite direction away from base portion 114. An adhesive pad is applied to each tab, as indicated at 122 and 124. The device further includes a pair of filter containers 126 and 128, each domain-shaped with a relatively wide generally annular bottom rim portion 130, and a large opening 132 at the top. Ellipsoidal filters 134 and 136 are shown beneath the containers.

Filters 134 and 136 are press-fit into containers 126 and 128, which in turn are inserted through respective openings 138 and 140 in panel 110 until the bottom rim portion 130 of each container is contiguous with one of base portions 112 and 114. The result is shown in FIG. 13. Broken lines in this figure illustrate how the flexible panel can be folded to direct tabs 118 and 120 upwardly. When the filters and containers are inserted into the nasal cavities, this positions the tabs along the lateral portions of the nasal walls. The adhesive pads are used to removably retain the tabs against the lateral nasal walls, to maintain panel 110 against the anterior nares and maintain filters 134 and 136 in the working position. In an alternative of this embodiment, self-supporting filters are used in lieu of the filter/container pairs.

Figure 15:
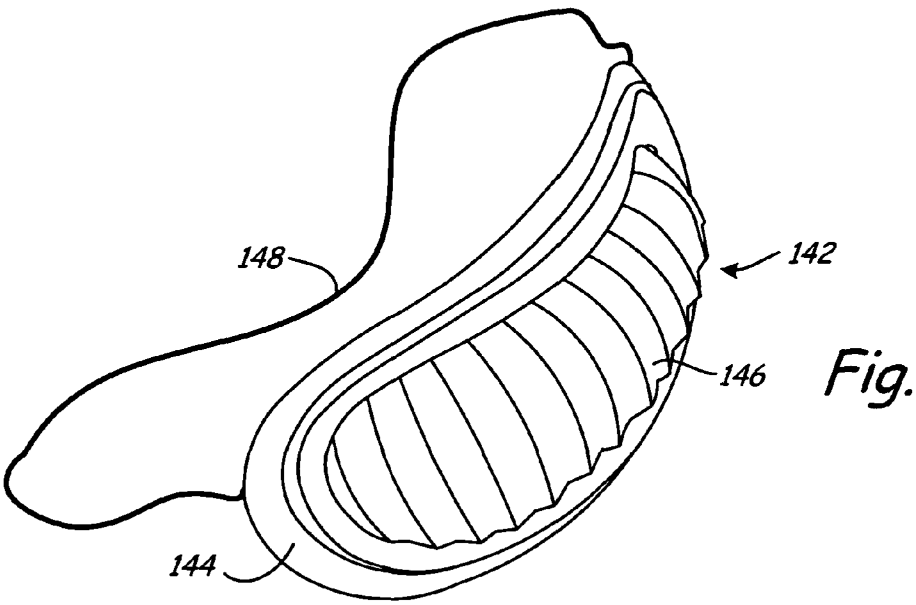
FIG. 15 is a perspective view of an air filtration device adapted to cover the mouth.

FIG. 15 shows a breathing air filtration device 142 designed to cover the mouth. The device includes a concave-convex base 144 with a concave surface designed to facilitate a close, preferably sealing surface engagement with the face of the user, in surrounding relation to the user's mouth. A filtering medium 146 is mounted to the base, secured to the base by an adhesive along its perimeter if desired. An elastic band 148 is secured at its ends to opposite sides of base 144. Filtering medium 146 is corrugated, and concave-convex with the outside or proximal side being convex.

Figure 16:
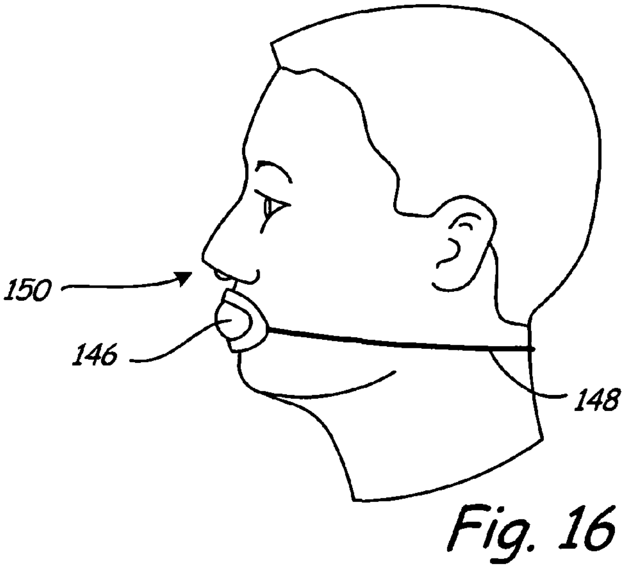
FIG. 16 is a side elevational view illustrating use of an alternative embodiment filtration system including the device of FIG. 15 in combination with a nasal filter.

As seen in FIG. 16, filtering device 142, in combination with one of the nasal filtering devices previously described, are worn in combination to provide an air filtration system 150 for use in lieu of a conventional mask filtration device covering the mouth and nose. As compared to a single mask, system 150 is less prone to leakage, due in part to the shorter and more consistent contour of the face in contact with base 144. Also, because band 148 is aligned with the mouth rather than the mouth and nose, it tends to assume a lower position around the neck and is less prone to downward slippage. System 150 encloses a volume of air near the mouth, but this volume is considerably less than the volume near the mouth and nose enclosed by a conventional mask. Thus, the volume available for entrapment of exhaled carbon dioxide is reduced. System 150 is adapted to virtually eliminate carbon dioxide accumulation altogether, by a user's inhaling exclusively through the nose. In addition to a better fit, system 150 is less prone to perimeter leakage.

Figure 17:
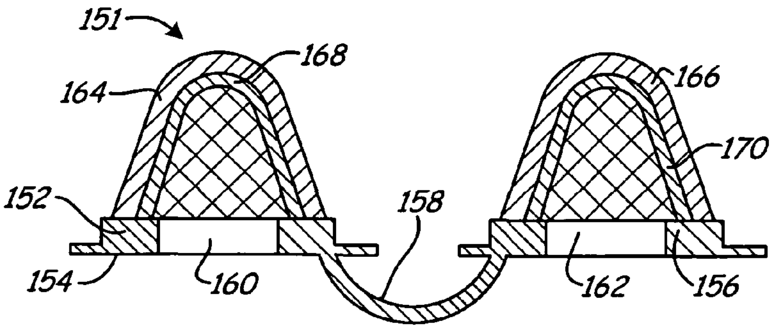
FIG. 17 is a schematic view of another alternative embodiment filtration device.

FIG. 17 illustrates another alternative embodiment filter, in the form of a two-stage nasal air filtering device 151. The device includes a flexible panel 152, including a base 154, an opposite base 156, and a bridge 158 connecting the bases in the same manner as the bridges in previous embodiments. Two generally elliptical openings are formed through the panel, including an opening 160 through base 154, and an opening 162 through base 156. In a manner similar to previous embodiments, base 154 supports an ellipsoidal filtering medium 164, and base 156 supports an ellipsoidal filtering medium 166. In addition, each of bases 154 and 156 supports an ellipsoidal preliminary screening filter: a screening filtering medium 168 in opening 160, and a screening filtering medium 170 in opening 162.

Device 151 provides two filtration stages, as inhaled air passes through one of filtering media 168 and 170, then through one of filtering media 164 and 166. In one preferred version, media 168 and 170 are relatively coarse activated charcoal filters, and filtering media 164 and 166 are finer (micropore) filters formed of polymeric fibers. Filters 168 and 170 screen out larger particles, and remove odors from the incoming air. This prevents the larger diameter particles from impacting and collecting over the ellipsoidal filters, lengthening their useful life.

Figure 18:
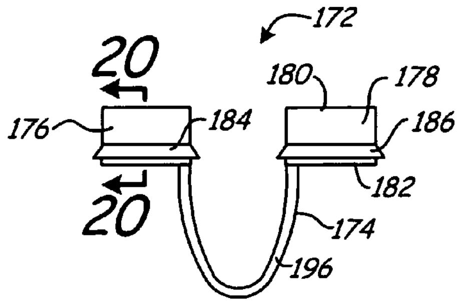
FIG. 18 is a forward elevational view of another alternative embodiment nasal air filtration device.
Figure 19:
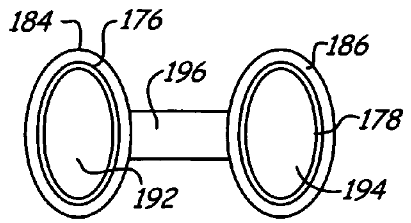
FIG. 19 is a top plan view of the device shown in FIG. 18.
Figure 20:
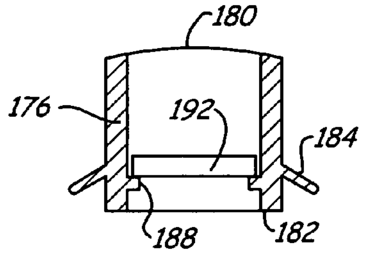
FIG. 20 is a sectional view taken along the line 20-20 in FIG. 18.
Figure 21:
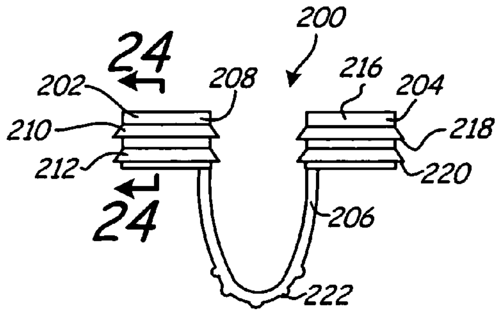
FIG. 21 is a forward elevational view of a further alternative embodiment nasal air filtration device.
Figure 22:
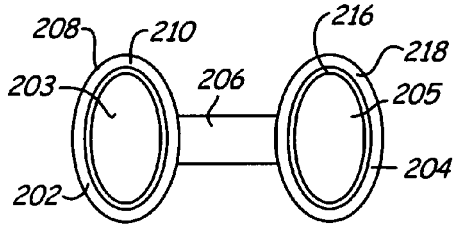
FIG. 22 is a top plan view of a device shown in FIG. 21.
Figure 23:
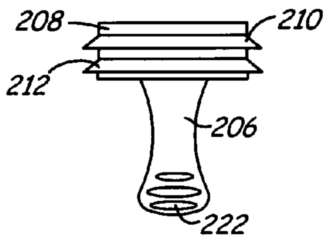
FIG. 23 is a side elevation of the device in FIG. 21.
Figure 24:
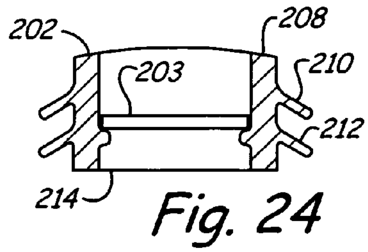
FIG. 24 is a sectional view taken along the line 24-24 in FIG. 21.

FIGS. 18-20 show a nasal air filtration device 172 including a filtering media support structure 174, preferably a unitary member formed of a flexible, biocompatible polymer having a relatively low durometer. One suitable material is thermoplastic elastomer available under the name "Santoprene" from Advanced Elastomer Systems, LP of Akron, Ohio. Another suitable material is available under the name "Dyna-Flex G2701-1000." The support device includes a pair of tubular bodies or sleeves 176 and 178. Each sleeve is arranged about a longitudinal axis, and as best seen in FIG. 19, has generally elliptical profiles in transverse planes. Each sleeve has an anterior end 180 and a posterior end 182. The sleeves are insertable into the nasal cavities by their anterior ends, so that in use the anterior ends are the distal ends in the sense of being disposed further into the nasal cavities.

A rim 184 runs circumferentially about sleeve 176 near posterior end 182. The rim is inclined, in that as it extends radially outward it also extends in the posterior direction, i.e. downward as viewed in FIGS. 18 and 20. Rim 184 has a substantially uniform thickness taken generally in the longitudinal direction. As an alternative, rim 184 can be tapered, with a thickness that gradually decreases in the radially outward direction.

Sleeve 178 is surrounded by a rim 186 substantially identical to rim 184 in its size, shape, incline, and location with respect to the posterior end of its associated sleeve.

Sleeves 176 and 178 are coupled to one another through a bridge 196. As in previous embodiments, the bridge determines the angular relationship of the sleeves and encounters the septum to limit sleeve insertion into the nasal cavities.

An annular interior ridge 188 projects radially inwardly from sleeve 176, and a similar ridge projects radially inwardly from sleeve 178. The ridges support filtering media 192 and 194, respectively. Media 192 and 194 are planar in the sense of being elliptical rather than ellipsoidal as in previously described embodiments. If desired, ellipsoidal or truncated-conical filtering media can be used to enhance the area available for filtration.

Media 192 and 194 may be formed from a wide variety of materials and may be formed with a wide range of porosities, depending on the nature of the contaminants to be filtered. Depending on the particles to be filtered by media 192 and 194, such as pollen, dust, bacteria, or viruses, as described in more detail below, the porosity may be selected accordingly. In one embodiment, the media are effective to prevent passage of particles greater than 10 microns diameter, and in another embodiment, the media prevent passage of particles greater than 5 microns. In yet another embodiment, the media are effective to prevent passage of particles greater than 3 microns, and in still yet another embodiment, the media prevent particles greater than 1 micron diameter. To filter viruses or other small particulates, as described in more detail below, appropriate media may be selected to prevent passage of particles as small as 0.675 microns, 0.375 microns, 0.328 microns, 0.2 microns, or even 0.1 micron. The selection of media material to achieve any of these levels of filtration may depend on the specific application of the device. Suitable materials for the media in accordance with the air filtration device of the present invention may include natural fabrics such as cotton, polymeric materials such as nylon, polyethylene and polypropylene, hypo-allergenic materials such as PVC and polyurethane, non-woven materials, adhesives, and statically charged or electrostatic material.

With respect to the rims and the ridges, it is to be appreciated that the terms "circumferential" and "annular" are used in the general sense to describe their continuous or endless nature, given that their transverse profiles are more elliptical than circular.

In use, each of sleeves 176 and 178 is inserted into one of the nasal cavities. Each of the rims is disposed inside its associated nasal cavity, and presses against surrounding tissue of the nasal wall and septum to support and maintain its associated sleeve within the cavity. Each rim further elastically conforms to the surrounding tissue along a generally annular region of its contact with the tissue, to form a seal which ensures that air entering the nasal cavity passes through the associated filtering medium. In this regard, rims 184 and 186 function like perimeter regions 20*a* and 22*a* of bases 20 and 22. Rims 184 and 186 also tend to maintain their respective sleeves spaced apart from the surrounding nasal tissue, in much the same manner as bases 20 and 22 maintain their respective filters.

The filtration device of the present invention may also function as a nasal dilator. In addition to the rims elastically conforming to the surrounding tissue of the nasal wall, it will be appreciated that the rims also can provide a desired expansion of the nasal breathing cavity. Specifically, due to both the sleeves 176/178 and the rims 184/186 having substantially elliptical profiles that substantially conform to nasal cavities, the inserted sleeves and rims will expand the nasal cavities thereby providing for greater and meliorated nasal breathing. In one embodiment, the rims and sleeves are arranged to cause the expansion to occur primarily at the base of the nasal passage, which avoids irritating other, more sensitive and irritable areas of the nasal cavity. This configuration also provides sufferers of swollen nasal membranes with immediate relief by allowing air to flow through the nasal chambers while simultaneously filtering out irritants. The benefits of expanding the nasal breathing cavities may be achieved by the rims with or without a filter. In use, the nasal device with a filter may provide substantial relief from a variety of ailments, such as the common cold. Common cold sufferers tend to have inflamed nasal tissue that is more vulnerable to continued attack from a variety of irritants, which may extend the duration of the cold symptoms. By simultaneously dilating the nasal cavity and protecting the inflamed tissue, inserting the nasal device may treat/relieve common cold symptoms.

Sleeves 176 and 178 and bridge 196 may each be formed of a transparent material that minimizes the visibility of the air filtration device 172 when worn. Other components of the device may also be formed of a transparent material to achieve the same goal, such as rims 184 and 186. Alternatively, various components of the device such as the sleeves, rims, and/or bridge may be formed of a material that changes color in response to environmental conditions. For instance, known materials change color when exposed to sufficient ultraviolet, or light at other wavelengths, or when exposed to sufficient moisture. Producing visible components of the filtration device from such materials may cause its appearance to change, for example, to an unattractive color subsequent to initial usage, thereby encouraging the wearer to obtain a replacement filtration device.

In addition, the incline and location of each rim affords several advantages. First, from FIG. 20 it is apparent that when sleeve 176 is inserted by anterior end 180 into the nasal cavity, any frictional drag due to contact of the rim with surrounding nasal tissue tends to bend rim 184 toward posterior end 182 of the sleeve. On the other hand, during removal of the sleeve from the nasal cavity, the same frictional drag tends to bend the rim toward anterior end 180.

Due to its incline and continuity (circumferential character), rim 184 is relatively easily bent radially inward and toward posterior end 182, but is much less inclined to bend radially outward and toward anterior end 180 due to the need for elastic expansion near the outer edge of the rim to accommodate the bend. Accordingly, rim 184 is configured to provide slight resistance to sleeve insertion and to provide substantial resistance to sleeve removal. As a result, sleeves 176 and 178 are easily and conveniently inserted into the nasal cavities for use, yet are effectively retained against accidental or inadvertent removal by rims 184 and 186.

Another difference from perimeter regions 20*a* and 22*a* is that rims 184 and 186 are recessed distally from the posterior ends of their respective sleeves. Consequently the rims are positioned further into the nasal cavities to provide better support during use, while the sleeve posterior ends remain more accessible to the user. This facilites a procedure in which a user who is wearing the filtration device readily can test the fit and seal of the device by placing fingers over the posterior ends of the sleeves, applying light pressure, and exhaling or inhaling. If no air seeps between rims 184/186 and the user's nasal tissue during this test, an airtight seal exists. In contrast, if the user senses air seepage between rims 184/186 and the user's nasal tissue during the test, a valid seal has not been formed. Where an airtight seal does not exist, the user may take corrective action or obtain a device of a different size. Where an airtight seal has been found during the test, the user may be assured that the seal created between filtration device and the user's nasal passage will likely remain unbroken during normal usage of the device. Such assurance not only provides confidence to the user who wears the device, but also it may reduce any potential liability of the device manufacturer, distributor, or others who are involved with providing the device, against claims of inadequate performance of the device.

FIGS. 21-24 illustrate an alternative embodiment nasal air filtration appliance or device 200 including a pair of support members 202 and 204 containing filtering media 203 and 205, and joined by a bridge 206. Support member 202 includes a tube or sleeve 208 similar to sleeve 176, a rim 210 disposed circumferentially about and extending radially outward from the sleeve, and a rim 212 similar to and longitudinally spaced apart from rim 210. Rims 210 and 212 preferably are inclined toward a posterior end 214, but need not be so inclined.

Support member 204 includes a sleeve 216 and longitudinally spaced apart rims 218 and 220, structured and configured like rims 210 and 212.

In general, each of rims 210, 212, 218 and 220 performs the same functions as rims 184 and 186 in the previous embodiment. The serial arrangement of a pair of rims on each sleeve, in lieu of a single rim, provides an improved seal and better retention of each sleeve within its associated nasal cavity.

Bridge 206 is similar to bridge 196 of the previous embodiment and performs the same functions. In addition, a series of ribs 222 are formed along bridge 206 to provide an improved gripping surface which is particularly useful for users wearing gloves or with soiled hands. Support members 202 and 204, including sleeves 208 and 216, and bridge 206 may each be formed of a transparent material that minimizes the visibility of the air filtration device 200 when worm. Other components of the device may also be formed of a transparent material to achieve the same goal, such as rims 210, 212, 218 and 220.

Figure 25:
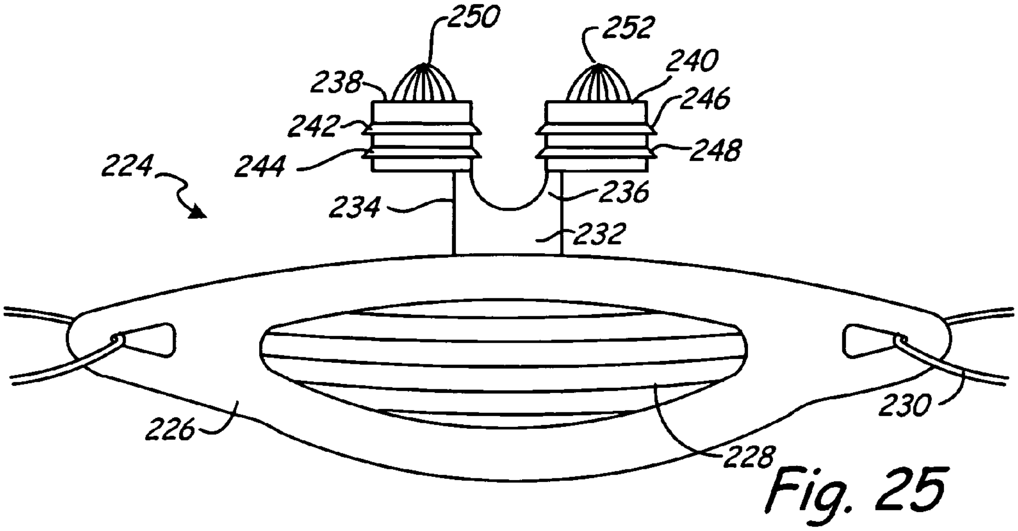
FIG. 25 is a forward elevation of a nose/mouth air filtration system constructed according to the present invention.
Figure 26:
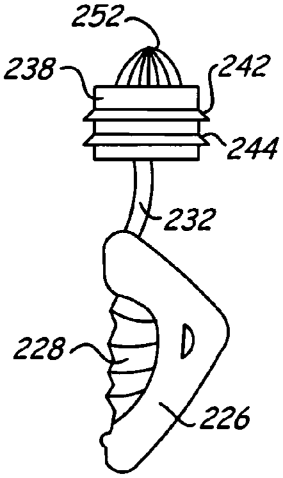
FIG. 26 is a side elevation of system shown in FIG. 25.

FIGS. 25 and 26 show a system 224 for filtering air entering the nose and mouth. System 224 includes a frame 226 shaped to facilitate a close, preferably sealing surface engagement with the face of the user, in surrounding relation to the mouth. A filtering medium 228, pleated for enhanced filtration surface area, is removably secured to frame 226 to enable disposal of the filters and reuse of the frame. An elastic band 230, shown only in part, is used to secure frame 226 against the face.

A connecting member 232 is integrally coupled to frame 226, and includes narrower portions 234 and 236 coupled to sleeves 238 and 240, respectively. The connecting member, along with supporting the sleeves relative to frame 226, determines their orientation and position with respect to each other.

A pair of longitudinally spaced apart rims 242 and 244 are disposed circumferentially about sleeve 238. Likewise, a pair of rims 246 and 248 surround sleeve 240. These rims form seals against surrounding nasal tissue when the sleeves are disposed within the nasal cavities. The rims also tend to support the sleeves within the nasal cavities, although support of the sleeves is provided primarily by frame 226 through connecting member 232.

A concave-convex filtering medium 250 is supported within sleeve 238. A similar filtering medium 252 is supported with sleeve 240. Like filtering medium 228, filtering media 250 and 252 are pleated to increase the surface area available for filtration. Also like filtering medium 228, concave-convex filtering media 250 and 252 can be disposable.

System 224 filters air inhaled through the nose or mouth, and thus functions in the manner of a conventional mask with a single perimeter that surrounds the nose and mouth. A primary advantage of system 224 is its close mounting proximity to the face. As compared to the conventional mask, system 224 provides a considerably reduced volume near the face for entrapment of exhaled carbon dioxide. In addition, system 224 forms a closer fit against the face and provides a more effective seal, due to the sealing action of the rims, the considerably reduced perimeter of frame 226 as compared to the perimeter of the conventional mask, and the portion of the face contacted by frame 226, which has a more consistent contour. If desired, a rim or pair of rims can be formed along the perimeter of frame 226, for surface engagement with the face to form a seal in much the same manner as the rims surrounding the sleeves.

Figure 27:
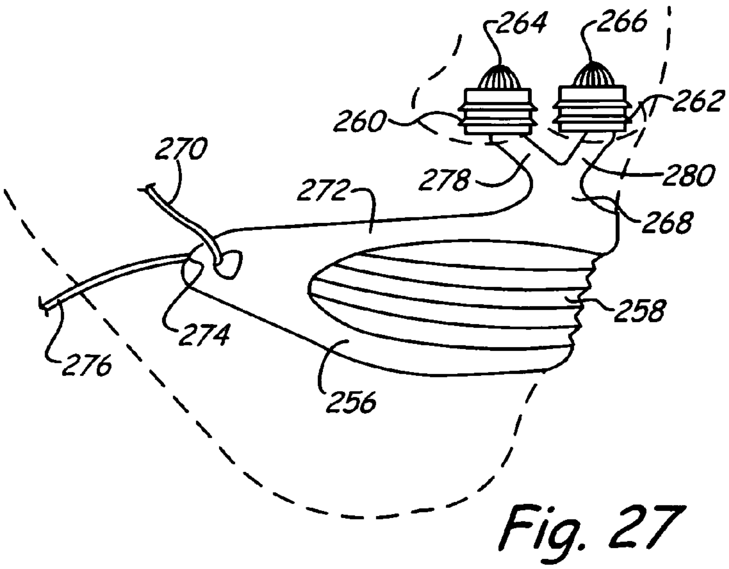
FIG. 27 is a perspective view of an alternative embodiment air filtration system.

FIG. 27 shows an alternative embodiment filtering system 254 similar to system 224 in providing a frame 256 adapted to surround the mouth, a pleated filtering medium 258 supported by the frame, sleeves 260 and 262 respectively supporting filtering media 264 and 268 insertable into the nasal cavities, and a connecting member 268 supporting the sleeves with respect to the frame and each other. An elastic band 270 maintains frame 256 against the face. Broken lines indicate the position of system 254 relative to the face and nose when in use.

In a departure from system 224, an upper portion 272 of frame 256 is modified to provide a fluid conduit running from one end 274 of the frame to its center. At end 274, the conduit is open to the exterior of the frame for coupling to a line 276, the other end of which is coupled to an oxygen supply (not shown). Connecting member 268 is modified to provide fluid conduits 278 and 280, in fluid communication with the frame conduit and open at their ends near sleeves 260 and 262, respectively. Thus, in demanding environments, system 254 can be used to provide a continuous supply of oxygen into the nasal passages, and is particularly effective when the user inhales through the nose and exhales through the mouth.

Several further features may be used to enhance any of the previously described devices and systems. The filtering media may be impregnated with constituents for therapeutic applications including aroma therapies, or to provide a cover aroma. Likewise, the polymer forming the sleeves and bridge may be scent-impregnated. The filtering media can be structurally reinforced by applying a fine polymeric mesh.

Thus in accordance with the present invention, a breathing air filtration device is insertable into the nasal cavities for improved, longer lasting filtration of inhaled air. The area available for filtration is enhanced by the concave-convex design of the filtering media, by forming pleats in the media, or by corrugating the media. Filtering is improved by a selective positioning of the filters and filter-supporting structures in spaced-apart relation to the surrounding nasal walls, resulting in more effective warming and moisturizing of the filtered air. Selectively inclined rims or rim pairs provide for convenient insertion while guarding against accidental or inadvertent removal of filtering media from the nasal cavities. The nasal filtering device also is effective in combination with an auxiliary filter covering the mouth, to provide a system suitable for use in lieu of a conventional mask, with improved resistance to perimeter leakage and accumulation of exhaled carbon dioxide.

In one use, the present invention may be implemented to address a variety of personal and health concerns. The present invention provides an effective means for providing allergy sufferers and individuals seeking personal health protection with relief from pollution, dust, allergens, and airborne diseases. For instance, allergic rhinitis, often called hay fever, is an overreaction of the immune system to particles in the air that a person breathes. The overreaction causes inflammation and symptoms that affect mainly the nose but also the eyes, ears, throat, and mouth. Recent studies have demonstrated that subjects wearing active nasal filters had significantly reduced symptoms. See, "The reduction of rhinitis symptoms by nasal filters during natural exposure to ragweed and gross pollen," Allergy, 2005: 60, pp. 529-532. The filters were shown to reduce symptoms of runny nose, itchy nose, sniffles, number of sneezes, itchy throat, itchy eyes, and water eyes.

In use, the air filtration device of the present invention may be worn by individuals to reduce or eliminate the effects of everyday inhalants such as dust, pollen, pollutants, mites, as well as bacteria, viruses, and other pathogens. For example, individuals who wish to reduce the effects of inhaling smog and other pollutants may wear an air filtration device of the present invention. The concern of pollution may be enhanced for individuals who frequently walk in urban environments, which may also be addressed by wearing an air filtration device of the present invention. Individuals with weakened immune systems, asthma, or allergic reactions to pollen and other allergens may use an air filtration device of the present invention to alleviate the reactions caused by allergens. Likewise, use of an air filtration device of the present invention may also prevent or reduce the risk of exposure to mold and epidemic outbreaks such as influenza and SARS.

Individuals performing common and routine activities may also implement a device of the present invention for other personal and health-related uses. For instance, the present invention may be worn by individuals performing various housework actions to reduce or prevent exposure to undesirable substances. An air filtration device of the present inventions may be worn by individuals working with bathroom and kitchen cleaners, window cleaners, furniture cleaners, and drain cleaners to reduce or prevent inhalation of chemicals found in such household cleaning products. The filtration device may also be worn while performing any other house cleaning, dusting, polishing, vacuuming, and window washing. Similarly, an air filtration device of the present invention may be used when changing furnace filters, cleaning fireplaces, cleaning wood stoves or ovens, changing cat litter, shaking rugs, or conducting air-pressure cleaning. An air filtration device of the present inventions may also be worn by individuals performing yard work, such as leaf raking, wood chopping, gardening and handling of different soils, fertilizers, and compost, lawn mowing, sidewalk and driveway sweeping and blowing, and bagging leaves, grass and other yard clippings, to reduce or eliminate inhalation of the dust created by these activities. Other household hold activities may also create dust and hazardous particles, which may be filtered by wearing an air filtration device of the present invention, including garage cleaning, leaf and rubbish burning, and house, fence, and building staining.

The air filtration device of the present invention may also be worn to address the inhalation of particles present during various hobbies and other common activities. Such hobbies may include fish and game cleaning and disposal, taxidermy, cooking with flour and other powdery substances, riding motorcycles, hiking, camping, and biking, particularly in pollenous areas, cleaning campfires and other camping activities, wood and metal work with drills and saws, sanding of wood, metal, and sheet rock, vacuuming and cleaning trucks, cars, boats, ATVs, and other vehicles.

In another use, the present invention may be implemented to filter undesirable inhalants in medical environments such as hospitals and health clinics, for both professionals and patients. Use of an air filtration device of the present invention filters bacteria, viruses, and other dangerous particles, including life-threatening toxins such as SARS and anthrax. In use, doctors, hospital and clinic workers, lab workers, other medical professionals, patients, and visitors may wear an air filtration device of the present invention to filter the air in medical environments, which may contain germs, viruses, microbial, bacteria, and the like. Air filtration devices of the present invention may also be implemented in medical environments to address specific epidemic outbreaks such as influenza, SARS, or the bird flu, including the H5N1 strain.

In yet another use, the present invention may be implemented to filter undesirable inhalants in construction and industrial environments. Occupational environments often subject individuals to products that are hazardous to inhale. An air filtration device of the present invention may be worn by individuals in factories or in the construction industry who may be exposed to solvents, chemicals, carcinogens, or toxins, or who are otherwise involved with activities such as concrete production, road construction, wiring installation and repair, insulation handling, plumbing, framing, venting, wall plaster installation or replacement, stucco cutting and repair, cutting stone, brick, or blocks, mixing mortar or dry cements, cutting and installing tile, other sanding and grinding, cutting and gluing plastic pipe PVC or ABS, drilling or grinding car cylinders, printing press or mill operation, or installation or handling of fiberglass, cellulose and various foam insulators.

Other occupations may also benefit from use of the air filtration device of the present invention, such as biologists, chemists, dentists and dental technicians, fire fighters, manicurists or salon workers who perform services such as hair dyeing and perming, mechanics and auto body technicians who perform brake work and the like, landscapers and gardeners involved with activities such as tree trimming and stump removal and construction of retaining walls, bulldozing, and handling of stone, timber, mortars wood chips, house cleaners, janitors, maids, sanitary sewer workers, waste management workers and other individuals who handle refuse, painters, dry cleaners, diesel truck drivers, road pavers, oil and gas refinery workers, gas station attendants, laundry cleaners, drain cleaners, daycare workers, warehouse workers, demolitionists, farmers, agriculturalists, harvesters, silo or silage workers, livestock handlers and stall cleaners, and miners. The air filtration device may be used to provide filtration for the wearer involved with other farm-related activities such as mowing, raking, baling and handling of hay and straw, horse cleaning, grooming, and handling, manure removal, and harvesting of wheat, soy beans, corn sugar beets, vegetables fruits, herbs or other produce. Other occupations for which a device of the present invention may be used include mailroom and other postal and package delivery workers, law enforcement and crime scene workers, customs and immigration workers, social workers, animal groomers, veterinarians, and morgue workers.

In still another use, the present invention may be implemented to filter undesirable inhalants in the air travel industry, by both airline employees and airline travelers. In use, an air filtration device of the present invention may be worn by air travel industry employees and passengers to filter out viruses, bacteria, life-threatening particles, and other undesirable inhalants, such as SARS and anthrax.

Air filtration devices of the present invention may also be implemented for a variety of environments relating to government and military uses or for addressing national security threats. In use, the device may be worn by military or government personnel to filter chemical or biological materials due to malicious or unintentional release of the materials. The device may also be worn civilians to protect against terrorist attacks or other security risks.

In yet another use, an air filtration device of the present invention may be used in a salon or spa environment for aroma-therapeutic purposes. A device of the present invention worn by spa and salon customers may include a filtering media that is impregnated with desirable constituents for therapeutic applications. Spa and salon employees may further use a device of the present invention to filter out other inhalants in their work environment.

What is claimed is:

1. A nasal air filtering device, comprising:

a first tubular body comprising an anterior end and a posterior end, and defining a first passageway therethrough, and further comprising a first rim and a second rim, wherein prior to insertion in a nasal cavity the first rim and the second rim are disposed circumferentially about the first tubular body and extend radially outwardly therefrom in the posterior direction at an acute angle with respect to the first tubular body;

a second tubular body comprising an anterior end and a posterior end, and defining a second passageway therethrough, and further comprising a third rim and a fourth rim, wherein prior to insertion in a nasal cavity the third rim and the fourth rim are disposed circumferentially about the second tubular body and extend radially outwardly therefrom in the posterior direction at an acute angle with respect to the second tubular body;

a first filtering medium and a second filtering medium disposed within the first tubular body and the second tubular body respectively; and a connecting member coupled to the first tubular body and the second tubular body;

wherein the first tubular body and the second tubular body are insertable by their respective anterior ends into associated nasal cavities with the rims being adapted to form a surface engagement with an interior of the nasal cavities; and wherein all rims of the first and second tubular bodies are longitudinally spaced from the posterior and anterior ends of their respective tubular bodies.

2. The nasal air filtering device of claim 1, wherein the connecting member comprises a transparent material.

3. The nasal air filtering device of claim 1, wherein the first tubular body and the second tubular body comprise a transparent material.

4. The nasal air filtering device of claim 1, wherein the first filtering medium and the second filtering medium are effective to prevent passage of particles greater than 0.1 micron in size through the first passageway and the second passageway.

5. The nasal air filtering device of claim 1, wherein the first filtering medium and the second filtering medium are effective to prevent passage of bacteria, viruses, and other pathogens through the first passageway and the second passageway.

6. The nasal air filtering device of claim 1, wherein the first filtering medium and the second filtering medium are effective to prevent passage of allergens and dust through the first passageway and the second passageway.

7. The nasal air filtering device of claim 6, wherein the first filtering medium and the second filtering medium are effective to prevent passage of pollen through the first passageway and the second passageway.

8. The nasal air filtering device of claim 1, wherein the first filtering medium and the second filtering medium are effective to prevent passage of pollutants through the first passageway and the second passageway.

9. The nasal air filtering device of claim 1, wherein the first filtering medium and the second filtering medium are effective to prevent passage of toxins through the first passageway and the second passageway.

10. The nasal air filtering device of claim 1, wherein the first filtering medium and the second filtering medium are effective to prevent passage of airborne particles capable of causing diseases through the first passageway and the second passageway.

11. The nasal air filtering device of claim 1, wherein the first filtering medium and the second filtering medium are effective to prevent passage of carcinogens through the first passageway and the second passageway.

12. The nasal air filtering device of claim 1, wherein the first filtering medium and second filtering medium have substantially elliptical profiles in transverse planes.

13. The nasal air filtering device of claim 1, wherein the first passageway and the second passageway, defined by the first and second tubular bodies respectively, have substantially elliptical profiles.

14. The nasal air filtering device of claim 1, wherein the rims are elastically deformable and tend to conform to the nasal cavities over areas of said surface engagement, to substantially form a seal along said areas and to support the first tubular body and the second tubular body within the nasal cavity.

* * * * *